United States Patent [19]

Myers et al.

[11] Patent Number: 4,987,237

[45] Date of Patent: Jan. 22, 1991

[54] DERIVATIVES OF MONOPHOSPHORYL LIPID A

[75] Inventors: Kent R. Myers, Hamilton, Mont.; Edgar F. Ribi, deceased, late of Hamilton, Mont., by Karin S. Ribi, personal representative

[73] Assignee: Ribi ImmunoChem Research, Inc., Hamilton, Mont.

[21] Appl. No.: 112,742

[22] Filed: Oct. 22, 1987

Related U.S. Application Data

[63] Continuation-in-part of Ser. No. 732,889, May 8, 1985, Pat. No. 4,866,034, which is a continuation-in-part of Ser. No. 526,967, Aug. 25, 1983, abandoned.

[51] Int. Cl.⁵ .................. C07F 9/655; C07F 9/6558
[52] U.S. Cl. .................. 549/222; 530/300; 530/322; 530/331; 536/17.7; 536/18.7; 536/117; 546/22; 548/119; 548/413; 548/414
[58] Field of Search ............... 549/222; 548/119, 413, 548/414; 546/22; 530/331, 300, 322; 536/17.7, 18.7, 117

[56] References Cited

U.S. PATENT DOCUMENTS 4,436,727  3/1984  Ribi .................................. 514/2
4,437,728  3/1984  Ribi et al. ........................ 514/2

OTHER PUBLICATIONS

"Peptides as Requirements for Immunotherapy . . ." E. Ribi et al., Cancer Immunology & Immunotherapy, 1979—pp. 43–58.
"Heterogeneity & Biological Activity . . ." C. Chen et al., Journal of Infect. Diseases, 1973—pp. S43–S51.
"Beneficial Modification . . ." E. Ribi, Jour. Bio. Rspn., pp. 1–9.
"Chem. Comb. of Biol. Active Der . . .", Hasegawa et al., 1986, pp. 371–385.

*Primary Examiner*—Richard L. Raymond
*Attorney, Agent, or Firm*—Burgess, Ryan & Wayne

[57] ABSTRACT

Novel derivatives of monophosphoryl lipid A and a process for their preparation are provided. The derivatives contain one or more free groups, such as an amine, on a side chain attached to the primary hydroxyl groups of the monophosphoryl lipid A nucleus through an ester group. The derivatives provide a convenient method for coupling the lipid A through coupling agents to various biologically active materials, substrates, and the like, wherein the immunostimulant properties of lipid A are desired.

11 Claims, No Drawings

DERIVATIVES OF MONOPHOSPHORYL LIPID A

RELATED APPLICATIONS

This application is a continuation-in-part of application Ser. No. 732,889 filed May 8, 1985, now U.S. Pat. No. 4,866,034, which is a continuation-in-part of application Ser. No. 526,967 filed Aug. 25, 1983, now abandoned. Both applications are incorporated herein by reference.

FIELD OF THE INVENTION

This invention relates in general to certain novel derivatives of monophosphoryl lipid A. In one aspect, this invention is directed to novel derivatives of monophosphoryl lipid A containing one or more substituted or unsubstituted amino groups. In another aspect, the invention relates to novel derivatives which are conjugates of monophosphoryl lipid A with certain biologically active materials. In a further aspect, this invention relates to methods for the preparation and use of the derivatives of this invention.

BACKGROUND OF THE INVENTION

Prior to the present invention, numerous reports have appeared in the literature which cited the reaction of lipopolysaccharide (LPS) with cyclic anhydrides, especially phthalic and succinic anhydride. However, with the exception of one reference, no mention has been made of combining monophosphoryl lipid A (MPL) with these or other anhydrides.

In an article by A. Hasegawa, et al, J. Carbohydrate Chem.5: 371, there is disclosed the covalent coupling of muramyl dipeptide (MDP) to a derivative of lipid A corresponding to the non-reducing glucosamine residue. This lipid A derivative, designated GLA-27 in the reference, was blocked at both the phosphate and at all other potentially reactive positions except for the hydroxyl to which coupling was desired (i.e. the primary hydroxyl at C6). The coupling strategy employed in this reference involved introducing a free carboxyl group into GLA-27 at C6 via succinic anhydride and a free amine into MDP, and then forming an amide linkage between these two groups. A key difference between the teachings of this reference and those of the present invention are that in the reference, the lipid A derivative had to be completely blocked in order to avoid side reactions during the condensation (i.e., amide bond forming) step. The present invention avoids this difficulty by introducing a free amino group into MPL. Coupling of MPL to other components is then achieved using reagents which react specifically with amines (e.g. aldehydes), or else activating an appropriate group on the other component prior to combining with the amino-MPL.

Acylation of lipopolysaccharides by cyclic anhydrides probably occurs in the O-antigen and core regions which are absent in monophosphoryl lipid A. The purpose of acylating LPS in these prior art references was to attenuate its toxicity, not to introduce a functional group for the purpose of forming covalent conjugates with other materials.

Accordingly, one or more of the following objects will be achieved by the practice of the present invention. It is an object of the invention to provide certain novel derivatives of monophosphoryl lipid A and a process for their preparation. Another object of this invention is to provide a novel process for the preparation of derivatives of monophosphoryl lipid A which does not require the blocking of any functional groups in order to introduce the desired groups into the molecule.

A still further object of the invention is to provide novel derivatives which are conjugates of monophosphoryl lipid A with biologically active materials such as antigens, antibodies, immunomodulators and the like. Another object is to provide novel conjugates of the derivatives with biological compounds such as antigens, which exhibit enhanced biological activity.

A further object of this invention is to provide a process for the preparation of derivatives of monophosphoryl lipid A in relatively pure form and substantially free of undesirable reaction by-products.

Another object of the invention is to provide methods for using the conjugates. These and other objects will readily become apparent to those skilled in the art in light of the teachings contained herein.

SUMMARY OF THE INVENTION

In its broad aspect, the invention relates to certain novel derivatives of monophosphoryl lipid A, certain intermediate compounds, a process for their preparation and use thereof. The novel derivatives are represented by the formula:

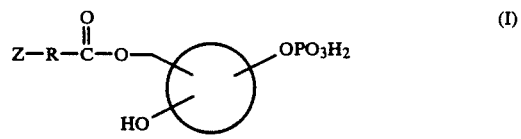

wherein, Z and R and the circle are as hereinafter defined.

These derivatives are conventionally prepared by reacting monophosphoryl lipid A with a compound containing a group or groups which is (are) predisposed to undergo a bond-forming reaction with a group or groups present in MPL. The use of a compound which is activated prior to the reaction with MPL avoids the necessity of first introducing protecting groups into the MPL molecule.

DETAILED DESCRIPTION OF THE INVENTION

Monophosphoryl lipid A (MPL) is a phosphorus-containing polyheterocyclic compound having pendant long chain, aliphatic ester and amide groups, and is obtained as an endotoxic extract from Enterobacteriaciae. The compound, also referred to as "MPL" is prepared in a manner set forth in U.S. Pat. Nos. 4,436,727 and 4,436,728 which are incorporated herein by reference. Endotoxin extracts of the type used as the starting material to produce MPL may be obtained from any Enterobacteriaciae including parent organisms and mutants. The aforesaid patents describe the type of microorganisms that may be used to obtain the starting material and several methods for preparing the starting material. MPL may also be prepared by synthetic and genetic engineering techniques. The preferred method to date of obtaining the endotoxic extract is that disclosed by Chen, et al, J. Infect. Dis. 128 543 (1973).

MPL is a composition characterized as having no detectable 2-keto-3-deoxyoctanoate, between about 350 and 475 nmoles/mg of of phosphorus and between about 1700 and 2000 nmoles/mg of fatty acids. Although the process for the preparation of refined detoxified endotoxin (MPL) was disclosed and claimed in the above-mentioned U.S. Pat. No. 4,436,727, the chemical structure was not fully known at that time and accordingly, it was necessary to describe MPL as a product-by-process. The complete structure of the hexaacyl form of MPL obtained from lipopolysaccharides of *Salmonella minnesota* R595 is now known and has been given as follows:

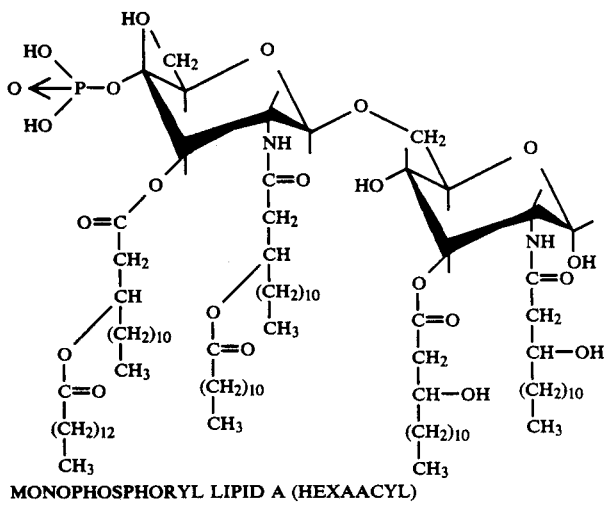

MONOPHOSPHORYL LIPID A (HEXAACYL)

MPL is a significant improvement over endotoxic extracts from Enterobacteriaciae because MPL is detoxified and therefore does not contain the highly toxic components which have rendered endotoxic extracts unsuitable for therapeutic use. (See *Peptides as Requirements for Immunotherapy of Guinea Pig Line-10 Tumor with Endotoxins*, Ribi, et al, Cancer Immunol. Immunother., Vol. 7, pp. 43–58, 1979, incorporated herein by reference.) The beneficial effects of MPL over other endotoxic extracts are described for example in U.S. Pat. Nos. 4,436,727 and 4,436,728 and in Ribi, E., Journal of Biological Response Modifiers, Vol. 3, pp. 1–9, 1984 (incorporated herein by reference). Due to the fact that the monophosphoryl lipid A is non-toxic, it has recently found application as an adjuvant for vaccines, and in other pharmaceutical compositions useful in the treatment of various disorders such as cancerous tumors in warm-blooded animals and the like.

The effectiveness of MPL as an adjuvant for certain antigens may be enhanced by coupling MPL directly to these antigens. In addition, covalent conjugates consisting of MPL and other immunopotentiating compounds may exhibit biological activities which are enhanced relative to the free (non-conjugated) components.

Traditional methods of forming covalent conjugates can be divided into two categories depending on whether the molecules are activated with respect to coupling prior to being mixed or are activated in situ after being mixed. Neither approach is feasible with unmodified MPL because of its structural configuration. For example, the prior activation approach entails introducing a group into one of the molecules which will react readily with a group present only in the second molecule such as an amino or a sulfhydryl. This approach is not feasible with unmodified MPL since it does not contain any functional groups which can be activated or which will react with groups previously activated on other molecules. The second approach also does not work with MPL since under the conditions generally employed for in situ activation, MPL tends to react with itself, which leads to a number of undesirable side products and greatly reduces or altogether eliminates the yield of the desired conjugate.

However, an appropriate functional group such as a primary amine can be incorporated into MPL by the method of the present invention; this allows normal coupling procedures to be employed for purposes of attaching other materials to the resulting modified MPL.

The functional groups which MPL contains include a primary hydroxyl at C-6', between 3 and 6 secondary hydroxyls and one phosphate group at C-4'. Due to the complex configuration of the monophosphoryl lipid A molecule and in order to simplify the reactions which occur in the process of the present invention, the monophosphoryl lipid A molecule will be depicted as:

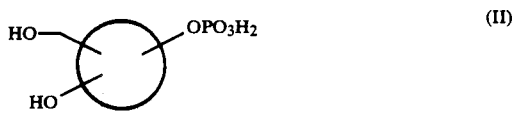
(II)

with the single primary hydroxyl shown at the top, a representative secondary hydroxyl at the bottom, the phosphate group shown by $OPO_3H_2$, and the circle representing the remainder of the monophosphoryl lipid A molecule.

As hereinbefore indicated, the derivatives of the present invention are conveniently represented by the formula:

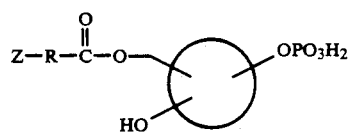

wherein Z represents hydrogen or the group:

wherein R represents a divalent group comprised of carbon, hydrogen and optionally, one or more of oxygen, nitrogen or sulfur and contains from 2 to 60 carbon atoms, preferably 2 to 20 carbon atoms; A represents a divalent coupling group which is capable of coupling R to Y through at least two independent functional groups, and wherein A contains from 2 to 60 carbon atoms and optionally, one or more of oxygen, nitrogen or sulfur; Y represents a biologically active material, such as antigens, antibodies, immunomodulators and the like; and n is zero or 1.

One embodiment of the present invention is directed to derivatives within the scope of the above general formula when Z is hydrogen. These monophosphoryl lipid A derivatives contain an ester side chain attached to the carbon atom of lipid A which bore the primary hydroxyl group (i.e., the C-6' carbon atom). The compounds can be represented by the formula:

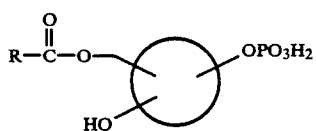
(III)

wherein R represents a group comprised of carbon, hydrogen and optionally, oxygen, nitrogen and/or sulfur, and contains from 2 to 60 carbon atoms, preferably 2 to 20 carbon atoms.

In general, any type of functional group can be introduced into MPL or related materials by the method of the present invention, provided that the functional group is part of a molecule that contains a carboxyl or similar group that can be activated toward ester bond formation prior to combination with MPL. Functional groups which can be introduced by this method include, but are not limited to, amines, thiols, aldehydes, carboxyls, N-hydroxyimido esters, imino esters, aryl azides, maleimides, pyridyl disulfides and active halogens.

This requirement of activation, prior to combining with MPL, is of key importance due to the numerous side reactions which can occur if MPL is exposed directly to activating conditions. An example of this prior activation approach is the reaction of MPL with succinic anhydride, which results in the introduction of a free carboxyl group into MPL.

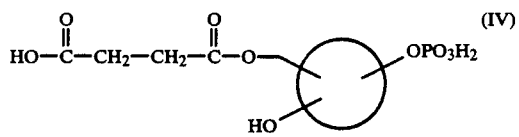
(IV)

Thus, derivatives such as those of Formula IV wherein R of Formula III terminates in a free carboxyl group and is attached through the ester group to the MPL molecule by means of an aliphatic, aromatic or heterocyclic group can be prepared in accordance with the teachings of the present invention.

It may or may not be necessary to block certain functional groups in the molecule which is to be introduced into MPL prior to the activation step. For example, in introducing an amino group into MPL by the method of the present invention, it is necessary to block the amine of an appropriate amino acid prior to activating the carboxyl for ester bond formation. In the example given above involving succinic anhydride, both the blocking and prior activation requirements are satisfied by formation of the cyclic anhydride. Suitable blocking and deblocking procedures are well known to those skilled in the art. See, for example, Theodora W. Green, "Protective Groups in Organic Synthesis", John Wiley & Sons, New York, 1981, pp. 349.

Preferred compounds which can be prepared by the process of the present invention are the amines and substituted amines which can be exemplified by the formula:

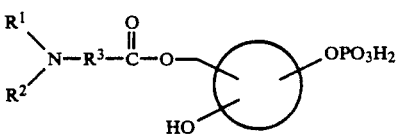
(V)

wherein $R^3$ represents a divalent chain which contains carbon, hydrogen and optionally oxygen, nitrogen and/or sulfur; and $R^1$ and $R^2$ individually represent hydrogen, or lower alkyl, or one of $R^1$ or $R^2$ can represent the residue of an organic substrate or carrier including liposomes, or a biological material such as an antigen, immunomodulator, antibody and the like.

Particularly refined compounds of Formula (V) are those wherein $R^1$ and $R^2$ are hydrogen and $R^3$ is a divalent radical of from 2 to 60, and more preferably 2 to 20 carbon atoms and is composed of carbon, hydrogen and optionally oxygen, nitrogen and/or sulfur. These derivatives include those wherein $R^3$ is a straight or branched hydrocarbon chain, and polypeptides containing one or more recurring amide groups, such as di- and tri-peptides of glycine derivatives of MPL. Included within these are those compounds wherein an amino acid is introduced into MPL at the C-6' position and accordingly, provide MPL derivatives having a side chain terminating in a primary amine. Typical compounds of this type include:

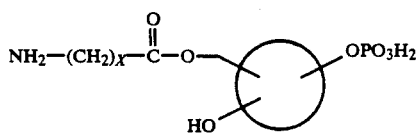
(VI)

wherein x can be equal to any value from 1 up to about 20, and higher. One example of this compound is when x = 5, which corresponds to the ester of 6-amino caproic acid. This compound is referred to as CAP-MPL and the synthesis is set forth in Examples 1-3.

Another compound of interest is the derivative where MPL is esterified to the free carboxyl end of peptides consisting of glycine or related alpha-amino acids. For example, the following compound consists of MPL esterified to a tripeptide of glycine:

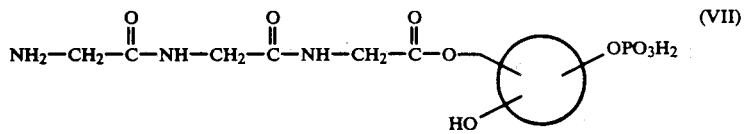

Accordingly, a variety of derivatives of MPL can be prepared from known amino acids. Alternative amino acids which can be introduced into the MPL molecule by the process of the present invention include, among others, glycine, alanine, serine, threonine, methionine, valine, norvaline, leucine, isoleucine, phenylalanine, tyrosine, crysteine, aspartic acid, glutamic acid, hydroxyglutamic acid, arginine, lysine, cystine, histidine, proline, hydroxyproline, tryptophan, asparagine, and glutamine. Suitable blocking and deblocking procedures well known to those skilled in the art may need to be employed when attaching these amino acids, or combinations thereof, to MPL by the process of the present invention.

Derivatives of MPL in which a primary amino group is introduced by the method of this invention can be further modified to a form which can be conveniently coupled to other compounds of interest, such as antigens, antibodies and immunomodulators. The general form of such MPL derivatives is as follows:

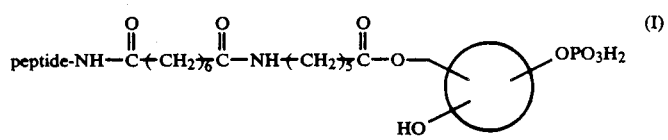

wherein $R^1$ and $R^3$ are as hereinbefore described; $R^2$ represents a group comprised of carbon, hydrogen and optionally oxygen, nitrogen and/or sulfur, and contains from 1 to 60 carbon atoms, preferably 1 to 20 carbon atoms; and $R^4$ represents a group which is able to form a covalent bond, either selectively with amines or sulfydryls or non-selectively with a wide variety of groups, and which is comprised optionally of carbon, hydrogen, nitrogen, oxygen and/or sulfur. The radical denoted by $R^4$-$R^2$ represent, for example, N-succinimidyl suberoyl, 6-(4'-azido-2'-nitrophenyl) hexanoyl, 3-(2-pyridyldithio propionoyl and m-maleimidobenzoyl. Example 4 describes the preparation of the following compound:

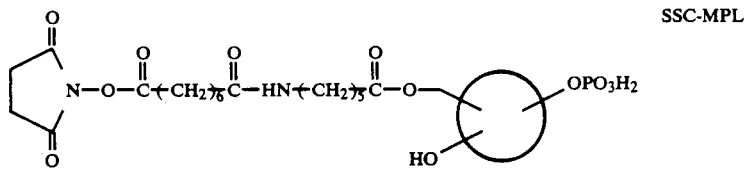

wherein $R_4$-$R_2$ represents N-succinimidyl suberoyl; and $R_1$ and $R_3$ correspond to the designation given in Formula VIII with X = 5.

Thereafter, the derivative comprised of MPL with a coupling group attached to MPL through an amine group, such as SSC-MPL above, is further reacted with a peptide containing a primary amine group to form a conjugate:

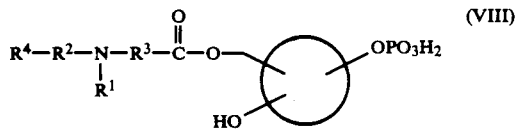

The process for preparing the present invention, as hereinafter described, provides a unique method for introducing one or more new functional groups into monophosphoryl lipid A and related compounds. These functional groups can provide a point of attachment for covalent coupling of MPL and related compounds to other materials of interest.

The process comprises the steps of:

(1) independently blocking the other functional group(s) of an appropriate carboxylic acid, if necessary;

(2) activating the free carboxyl of the blocked compound with respect to ester bond formation;

(3) reacting the activated acid with monophosphoryl lipid A; and (4) de-blocking the resulting MPL derivative, if necessary.

The process of the invention can be illustrated by the following sequence of reactions wherein an amino-MPL derivative of the type represented by Formula IV is prepared. In this sequence, t-BOC-ON represents t-butoxycarbonyloxyimino-2-phenylacetonitrile and MPL is as depicted above:

(1) Blocking

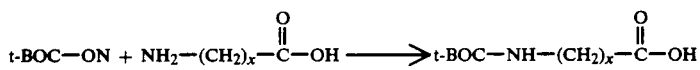

(2) Activation

(3) Reaction with MPL

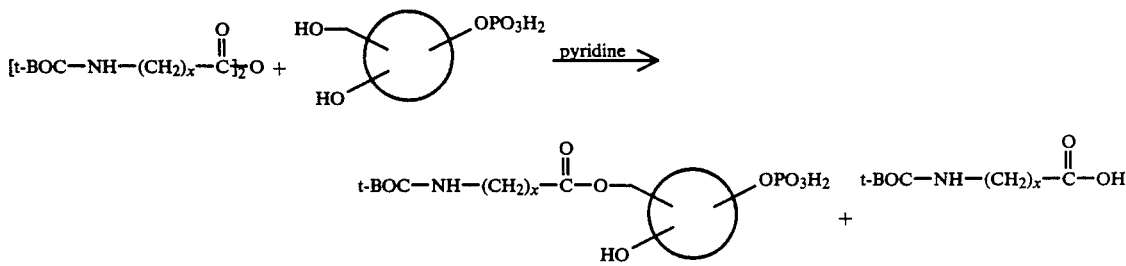

(4) De-blocking

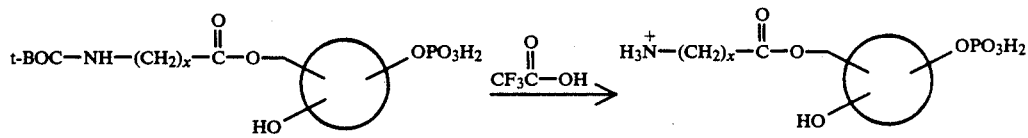

Although t-BOC-ON is employed in the above reaction as the blocking agent in step (1), other agents can be used as well. Typical blocking agents include, but are not limited to, benzyl chloroformate, 9-fluorenylmethyl chloroformate and 2,2,2-trichloromethyl chloroformate.

The blocking of amino acids or other compounds is effected in an appropriate solvent such as water, ethanol or dioxane, and at temperatures of from about 0° C. to about 30° C., depending upon the nature of the blocking agent.

Activation of the blocked acid in step (2) to form the anhydride can be accomplished using a compound such as dicyclohexylcarbodiimide or other compounds such as 1-ethyl-3-(3-dimethylaminopropyl)carbodiimide and ethyl chloroformate. This step is carried out in the presence of an inert solvent such as chloroform or dichloromethane, and at a temperature of from about 0° C. to 30° C., depending on the reagent which is used.

Reaction of the anhydride with MPL in the third step is accomplished in a solvent mixture, such as pyridine:chloroform 1:1 (V/V), and at a temperature of from about 0° C. to about 30° C.

De-blocking of the amino acid or other compounds introduced into the MPL molecule can be effected using a de-blocking agent such as trifluoroacetic acid or hydrogen chloride (gas)in an appropriate solvent at temperatures within the range of from about −15° C. to about 0° C.

As previously discussed, the process of this embodiment of the present invention is particularly useful and provides a unique method for introducing free amino groups into monophosphoryl lipid A and related compounds where other functional groups prevent the direct use of standard coupling agents such as carbodiimides. For example, MPL contains a phosphate group, a primary hydroxl, and several secondary hydroxyls. In the presence of carbodiimides or other condensing agents, side reactions leading to phosphoric anhydrides, phosphate esters, and other materials occur. The process of the present invention avoids such side reactions and accordingly provides a process for preparing the desired derivatives in relatively pure form.

In a further embodiment, the present invention is directed to derivatives of monophosphoryl lipid A, wherein a coupling agent has been attached to the compound of formula (III) to provide a derivative of the formula:

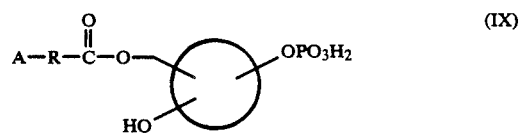

(IX)

wherein R is as hereinbefore defined, and A represents a coupling group through which attachment may be made to the Y group as previously indicated.

Illustrative A groups which can be employed in the present invention include, but are not limited to, the N-succinimidyl suberoyl group, the 6-(4'-azido-2'-nitrophenyl) hexanoyl group, the 3-(2-pyridyldithio)-propionoyl) group, the m-maleimidobenzoyl group, and the like.

The reaction of the coupling agents with the compounds of formula (III) can be effected by known techniques and the particular choice of conditions will vary according to the particular reactants employed.

In another embodiment of this invention, derivatives of monophosphoryl lipid A are provided which are comprised of the compound of formula (III) above, coupled through the divalent A groups to biologically active materials. These derivatives hereinafter also referred to as "conjugates" can be represented by the formula:

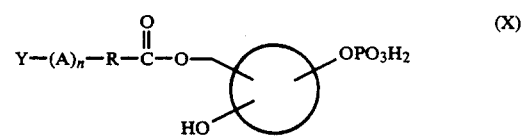

(X)

wherein A and R are defined above and Y represents a biologically active material. Such compounds combine in one molecule the properties of both the biological material and the monophosphoryl lipid A.

Illustrative biological materials which can be coupled to the MPL derivative of formula (III) through a coupling agent, include, but are not limited to: immunopotentiators, such as, Tuftsin, muramyl dipeptide, cell wall skeleton, trehalose dimycolate, and the like; cytokines, such as, interleukins, interferons, granulocyte-monocyte activating factor, tumor necrosis factor, and the like; antigens, such as, relating to infectious disease; tumor-specific antibodies; membranes, such as phospholipid membranes, including membranes composing structures such as liposomes, and carriers, supports, such as latex beads, dextran, cellulose resins, and the like.

The immunopotentiator, tuftsin, indicated above, and in the examples, is the compound, L-threonyl-L-lysyl-L-prolyl-L-arginine. Its pharmacologically acceptable salts and derivatives, and certain of its optical isomers are useful for stimulating or inhibiting phagocytosis or pincytosis in mammals. Other therapeutically useful non-antigenic polypeptides include: L-thr-L-lys-L-pro-L-arg-L-thr-L-lys-L-pro-L-arg,D-thr-L-lys-L -pro-D-arg-D-thr-L-lys-L-pro-D-arg, D-thr-L-lys-L-pro-L-arg-L-thr-L-lys-L-pro-D-arg and pharmacologically acceptable salts and derivatives thereof.

The coupling of the biologically active component to the MPL derivative of formula (IX) above can be effected by known reactions set forth in the literature. In some instances, and depending upon the functional groups available on the R moiety, it may be possible to directly link the biologically active component Y directly to R, and in such instance n in formula (X) above will be zero.

As previously indicated, monophosphoryl lipid A is an immunostimulant and when coupled to other compounds having desirable biological properties may impart enhanced biological activity to such compounds. For example, the effectiveness of MPL as an adjuvant for antigens may be enhanced when the antigen is coupled to MPL by employing the derivatives of the present invention. These conjugates may have utility as more potent immunopotentiating compounds, better adjuvants for relatively non-immunogenic antigens, and as tools for immunological research. The conjugates of the formula indicated above, are accordingly useful in the detection of various biological components contained in body fluids, such as blood, urine and also in biological research. Conjugates, such as those of monophosphoryl lipid A conjugated to immunopotentiators or cytokines are useful in the stimulation of specific and non-specific immune response. Conjugates, having antibodies coupled to MPL are useful in the stimulation of a specific immune response, in affinity chromatography, immunoassays, cellular adsorption onto solid supports and the like. Conjugates having antigens coupled to MPL are also useful in the stimulations of a specific immune response. MPL can also be conjugated to carriers for use in biological research and testing.

The following examples illustrate the best mode presently contemplated for the preparation of the derivatives of the present invention.

EXAMPLE 1

Synthesis of N-t-Butoxycarbonyl-6-Aminocaproic Anhydrides (t-BOC-CAP Anhydride)

N-t-Butoxycarbonyl-6-aminocaproic acid (t-BOC-CAP) was prepared from t-butoxycarbonyloxyimino-2-phenylacetonitrile (BOC-ON) and 6-aminocaproic acid, following the method of W. J. Paleveda, F. W. Holly, D. F. Veber, Organic Syntheses 63, 171 (1984). 100 mg ($4.32 \times 10^{-4}$ mole) of the resulting t-BOC-CAP was converted to the anhydride by treatment with 50 mg ($2.42 \times 10^{-4}$ mole) of dicyclohexylcarbodiimide in dry $CHCL_3$. Following the usual work-up procedures and recrystallization from diethyl ether/hexane, 76 mg of t-BOC-CAP anhydride was obtained. (IR-3480, 1821, 1751, 1719 $cm^{-1}$; $^1$H-NMR - no carboxyl proton).

EXAMPLE 2

Synthesis of (N-t-Butoxycarbonyl-6-Aminocaproyl)-Monophosphoryl Lipid A (t-BOC-CAP-MPL)

To a 100 ml round bottom flask was added 410 mg (approx. $2.7 \times 10^{-4}$ mole) monophosphoryl lipid A dissolved in chloroform:methanol 4:1 (v/v). The solvent was removed by flash evaporation, and the flask was left on a lyophilizer overnight to remove the final traces of solvent and moisture. To the dried residue was added 171 mg t-BOC-CAP anhydride ($3.84 \times 10^{-4}$ mole) and 12 mls each of chloroform and pyridine, both of which had been dried over 4A molecular sieves. The reaction mixture was stirred under nitrogen. The progress of the reaction was monitored by thin layer chromatography (TLC) on silica gel 60 TLC plates (EM), using a solvent system consisting of chloroform:methanol:water:ammonium hydroxide 50:31:6:2 (v/v). Developed TLC plates were visualized by spraying with 7% phosphomolybdate in ethanol followed by charring at 150° C. The reaction appeared to be complete after the first 24 hours. The reaction was stopped after 52 hours by adding 30 mls 0.10 M $Na_2CO_3$ (pH 10) and stirring vigorously for 30 minutes. The mixture was then transferred to a separatory funnel, 12 mls each of chloroform and methanol were added and the funnel was shaken. The organic phase was withdrawn, and the aqueous phase was extracted again with another portion of chloroform:methanol 2:1 (v/v). The organic phases were combined and washed with 1N HCl until an acidic pH was obtained in the aqueous phase (required 210 mls). The organic phase was washed once with water, then flash evaporated and taken to final dryness on a lyophilizer. The weight of the resulting residue was 491 mg.

EXAMPLE 3

Converting t-BOC-CAP-MPL to CAP-MPL 468 mg of t-BOC-CAP-MPL was dried in a 50 ml round bottom flask, using a lyophilizer to remove the final traces of solvent and moisture. The flask was then equipped with a magnetic stir bar and placed in a dry ice/ethylene glycol bath ($-15°$ C.). To the flask was added 20 mls cold trifluoracetic acid (TFA) which had previously been dried by vacuum distillation off of $P_2O_5$ (distillation flask at $-15°$ C., receiving flask at $-77°$ C.). The reaction solution was stirred vigorously for 20 minutes, after which time the TFA was removed by distillation. The final traces of TFA were chased with chloroform, resulting in 450 mg of a glassy reddish-brown residue.

The crude product mixture was fractionated by ion-exchange chromatography on a $2.5 \times 20$ cm column of DEAE cellulose in the acetate form (Indion HA-3). After loading with 447 mg of crude CAP-MPL, the column was rinsed with 220 mls each chloroform:methanol 4:1 (v/v) and chloroform:methanol:water 2:3:1 (v/v), and then eluted with a linear salt gradient composed of 900 mls of chloroform:methanol:water 2:3:1 (v/v) against 900 mls of chloroform:methanol:0.2M ammonium acetate 2:3:1 (v/v). A total of 312 mg of monosubstituted CAP-MPL was obtained in the 4:1 and 2:3:1 foreruns. Another 116 mg of material, corresponding primarily to unreacted MPL, was recovered during the salt gradient elution.

Further fractionation of CAP-MPL into single components was carried out on silica gel (BioSil HA), using a linear gradient of 1000 mls chloroform against 1000 mls chloroform:methanol:water 590:400:10 (v/v). The fractions corresponding to the hexaacyl homolog of CAP-MPL were pooled and subjected to further purification on 500 micron silica gel H preparative TLC plates (Analtech), using chloroform:methanol:water:ammonium hydroxide 50:31:6:2 (v/v) as the developing solvent. Mass spectral analysis of the resulting purified hexaacyl CAP-MPL revealed a single component with a m/e of 1830, corresponding to the expected mass for hexaacyl MPL combined with one 6-amino caproyl group.

EXAMPLE 4

Synthesis of (N-Succinimidyl suberoly)-CAP-MPL (SSC-MPL)

Into a 4 ml screw cap vial was placed 14.8 mg hexaacyl CAP-MPL ($8.09 \times 10^{-6}$ mole). The vial was charged with 1.0 ml dry chloroform which had been stored over 4A molecular sieves. To the chloroform solution of CAP-MPL was added 12.6 mg di-(N-succinimidyl) suberate (Pierce Chemical Co.; $3.23 \times 10^{-5}$ mole), followed by 1.0 ml pyridine (4A sieves) and a flea bar. The vial was tightly capped, then stirred at room temperature (24° C.) for several hours until the reaction was judged complete by TLC. (The product migrates with an $R_f$ of about 0.49 under the TLC conditions given in Example 2.) At this point, all solvent was removed by flash evaporation, using an aspirator to remove the chloroform and a vacuum pump to remove the pyridine. The temperature was kept below 40° C. at all times. The resulting residue was transferred to a 30 ml Corex tube using a minimal amount of chloroform, and product was precipitated by the addition of 20 ml acetone while vortexing. The precipitate was pelleted by centrifuging at $12,000 \times g$ for 20 minutes. The pellet was suspended in 20 ml acetone and then centrifuged again at $12,000 \times g$ for 20 minutes. The pellet fraction, after evaporation of the last traces of solvent, yielded 10.7 mg of product. (IR-1780 (w), 1810 (w) $CM^{-1}$; TLC - $R_f=0.49$ on silica gel 60, using chloroform:methanol:water:ammonium hydroxide (50:31:6:2)).

EXAMPLE 5

Coupling of SSC-MPL to Tuftsin (Thr-Lys-Pro-Arq)

10.1 mg partially purified SSC-MPL was dried into a 5 ml round bottom flask, resulting in a thin, clear film. 16.7 mg tuftsin (Sigma; $3.34 \times 10^{-5}$ mole) was dissolved in 1.37 ml 100 cm HEPES buffer at pH 7.85, which had been prepared by titrating the free acid form of HEPES (Sigma) with triethylamine. The total quantity of the aqueous tuftsin solution was added to the flask, along with a $10 \times 3$ mm magnetic stir bar, and the solution was vigorously stirred overnight. The solution was occasionally submitted to brief (ca. 10 seconds) sonication in an ultrasonic bath to facilitate disruption of the SSC-MPL film. After 24 hours, the solution was transferred to a dialysis bag (cutoff—6000-8000 MW) and dialyzed exhaustively against distilled water. The resulting dialysate was lyophilized, ultimately yielding 12.3 mg of a white powder. (TLC - $R_f=0.12$, 0.21 (major) and 0.45 (minor) on silica gel 60, developed with chloroform:methanol:water 65:25:4. SSC-MPL migrates at $R_f=0.53$ in this TLC system.)

The crude product mixture was fractionated by preparative TLC on 500 micron silica gel H prep plates (Analtech), using the 50:31:6:2 solvent system to develop the plates. Bands were visualized by backlighting, and the products were recovered by standard techniques. Two relatively pure product bands were recovered, corresponding to $R_f=0.12$ (2.3 mg) and $R_f=0.21$ (4.5 mg) in the 65:25:4 TLC system.

EXAMPLE 6

Synthesis of Succinoyl-MPL

To a 2.0 ml screw-cap vial was added a chloroform:methanol 4:1 (v/v) solution containing 29 mg ($1.68 \times 10^{-5}$ mole) hexaacyl MPL. All solvent was evaporated, the final traces being removed on a lyophilizer. 3.4 mg ($3.36 \times 10^{-5}$ mole) succinic anhydride was weighed into the vial and a flea bar was added, followed by 0.2 ml each of chloroform and pyridine which had been dried by storing over 4A molecular sieves. The solution was stirred for 5 hours, then transferred to a 15 ml Corex centrifuge tube and quenched by stirring with 1.0 ml 0.1 M $Na_2CO_3$ (pH 10.0) for minutes. 2 mls chloroform and 1 ml methanol were added to the quenched reaction, and it was centrifuged at 3,000 rpm for 10 minutes to separate the phases. The organic layer was then washed 2 times with 1N HCl, one time with water, and evaporated under a stream of nitrogen to yield 27.4 mg of a glassy residue. As estimated by silica gel TLC (see Example 2, above), this material consisted of 50% mono-succinyl-MPL, 20% di-succinyl-MPL, and 30% unreacted MPL.

Although the invention has been illustrated by the preceeding examples it is not to be construed as being limited to the materials employed therein; but rather, the invention encompasses the generic area as hereinfore disclosed. Various modifications and embodiments can be made without departing from the spirit or scope thereof.

What is claimed is:

1. A derivative of monophosphoryl lipid A having the formula:

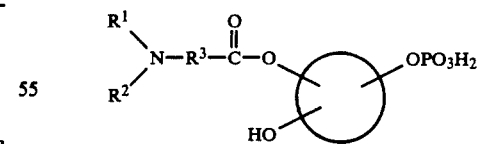

wherein $R^1$ and $R^2$ are hydrogen, $R^3$ is a straight or branched hydrocarbon chain composed of carbon, hydrogen, and optionally oxygen, nitrogen and sulfur which if more than one atom may be the same or different, wherein the total number of carbon atoms does not exceed 60, and the circle represents a monophosphoryl lipid A nucleus.

2. A derivative of monophosphoryl lipid A having the formula:

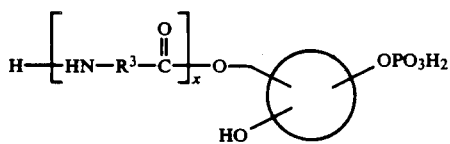

wherein the segment of the derivative represented by:

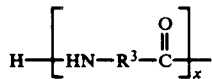

contains 2–60 carbon atoms and wherein $R^3$ is a straight or branched hydrocarbon chain composed of carbon, hydrogen, and optionally oxygen, nitrogen and sulfur which if more than one atom may be the same or different, and x is a minimum of 1 and can be any whole number such that the total number of carbon atoms of all x segments does not exceed 60, wherein the chemical structure of each $R^3$ may be the same or different in each such segment and wherein the circle represents a monophosphoryl lipid A nucleus.

3. The derivative of claim 1, wherein the total number of carbon atoms in $R^3$ does not exceed 20.

4. The derivative of claim 2, wherein the segment of the derivative represented by:

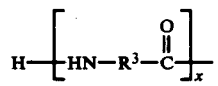

contains 2–20 carbon atoms and wherein $R^3$ is as indicated and wherein x is a minimum of 1 and can be any whole number such that the total number of carbon atoms of all x segments does not exceed 20, and wherein the chemical structure of each $R^3$ may be the same or different in each such segment.

5. The derivative of claim 2, wherein the segment of the derivative represented by:

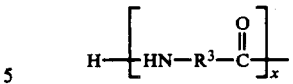

is an alpha-amino acid residue and wherein when the value of x is greater than 1, the alpha amino acid residue in each such segment may be the same or different.

6. The derivative of claim 4, wherein the segment of the derivative represented by:

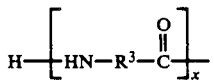

is an alpha-amino acid residue and wherein when the value of x is greater than 1, the alpha-amino acid residue in each such segment may be the same or different.

7. The derivative of claim 3, having the formula:

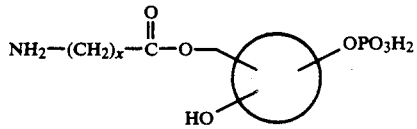

wherein x is 5 and the circle represents a monophosphoryl lipid A nucleus.

8. The derivative of claim 5, wherein the alpha-amino acid residue is selected from the group consisting of glycine, alanine, methionine, valine, norvaline, leucine, isoleucine, phenylalanine and lysine.

9. The derivative of claim 6, wherein the alpha-amino acid residue is selected from the group consisting of glycine, alanine, methionine, valine, norvaline, leucine, isoleucine, phenylalanine and lysine.

10. The derivative of claim 9, wherein the alpha-amino acid residue is glycine.

11. The derivative of claim 9, wherein the alpha-amino acid residue is lysine.

* * * * *

UNITED STATES PATENT AND TRADEMARK OFFICE
CERTIFICATE OF CORRECTION

PATENT NO. : 4,987,237

DATED : January 22, 1991

INVENTOR(S) : Kent R. Myers, et al

It is certified that error appears in the above-identified patent and that said Letters Patent is hereby corrected as shown below:

Column 3, that portion of the formula appearing after line 9 and reading:

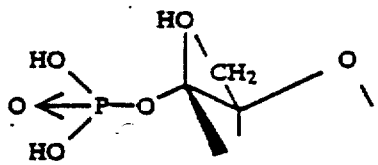

should read

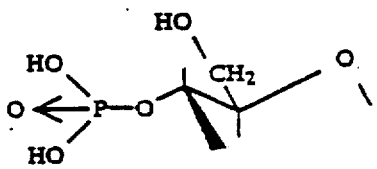

UNITED STATES PATENT AND TRADEMARK OFFICE
CERTIFICATE OF CORRECTION

PATENT NO. : 4,987,237
DATED : January 22, 1991
INVENTOR(S) : Kent R. Myers, et al It is certified that error appears in the above-identified patent and that said Letters Patent is hereby corrected as shown below:

Column 14, line 55; the formula should read as follows:

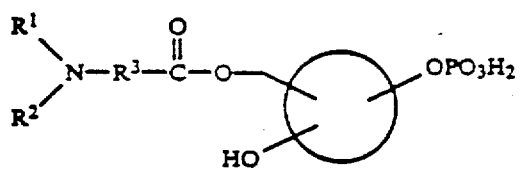

Signed and Sealed this

Twenty-first Day of July, 1992

Attest:

DOUGLAS B. COMER

Attesting Officer      Acting Commissioner of Patents and Trademarks